United States Patent [19]

Sy

[11] 4,356,336
[45] Oct. 26, 1982

[54] PURGING OF INERTS IN CHLORINATED HYDROCARBON PRODUCTION

[75] Inventor: Angel Sy, Cedar Park, N.J.

[73] Assignee: The Lummus Company, Bloomfield, N.J.

[21] Appl. No.: 915,895

[22] Filed: Jun. 15, 1978

[51] Int. Cl.³ .......................................... C07C 17/152
[52] U.S. Cl. ................................... 570/243; 570/244; 570/224; 570/225
[58] Field of Search .................... 260/659 A, 659 R; 423/481, 500, 488; 570/243, 244, 224, 225

[56] References Cited

U.S. PATENT DOCUMENTS

| | | | |
|---|---|---|---|
| 3,879,481 | 4/1975 | Sze et al. | 260/654 R |
| 3,950,443 | 4/1976 | Prahl | 260/659 A |
| 3,992,460 | 11/1976 | Tsao | 260/654 R |
| 4,018,879 | 4/1977 | Winnen | 423/481 |
| 4,071,571 | 1/1978 | Tsao | 260/659 R |
| 4,071,572 | 1/1978 | Amato et al. | 260/659 A |
| 4,073,871 | 2/1978 | Optiz et al. | 423/481 |
| 4,125,593 | 11/1978 | Scheifley et al. | 423/481 |

Primary Examiner—Charles F. Warren
Assistant Examiner—Joseph A. Boska
Attorney, Agent, or Firm—Elliot M. Olstein; Louis E. Marn

[57] ABSTRACT

In the production of a chlorinated hydrocarbon, such as chlorinated methanes, a purge stream is recovered from the chlorinated hydrocarbon effluent, which contains inerts and unreacted hydrocarbon. The unreacted methane present in the purge stream is combusted to recover the fuel values thereof; e.g., as a fuel in the waste chlorinated hydrocarbon combustion to recover chlorine values, with the inerts then being purged from the system.

7 Claims, 1 Drawing Figure

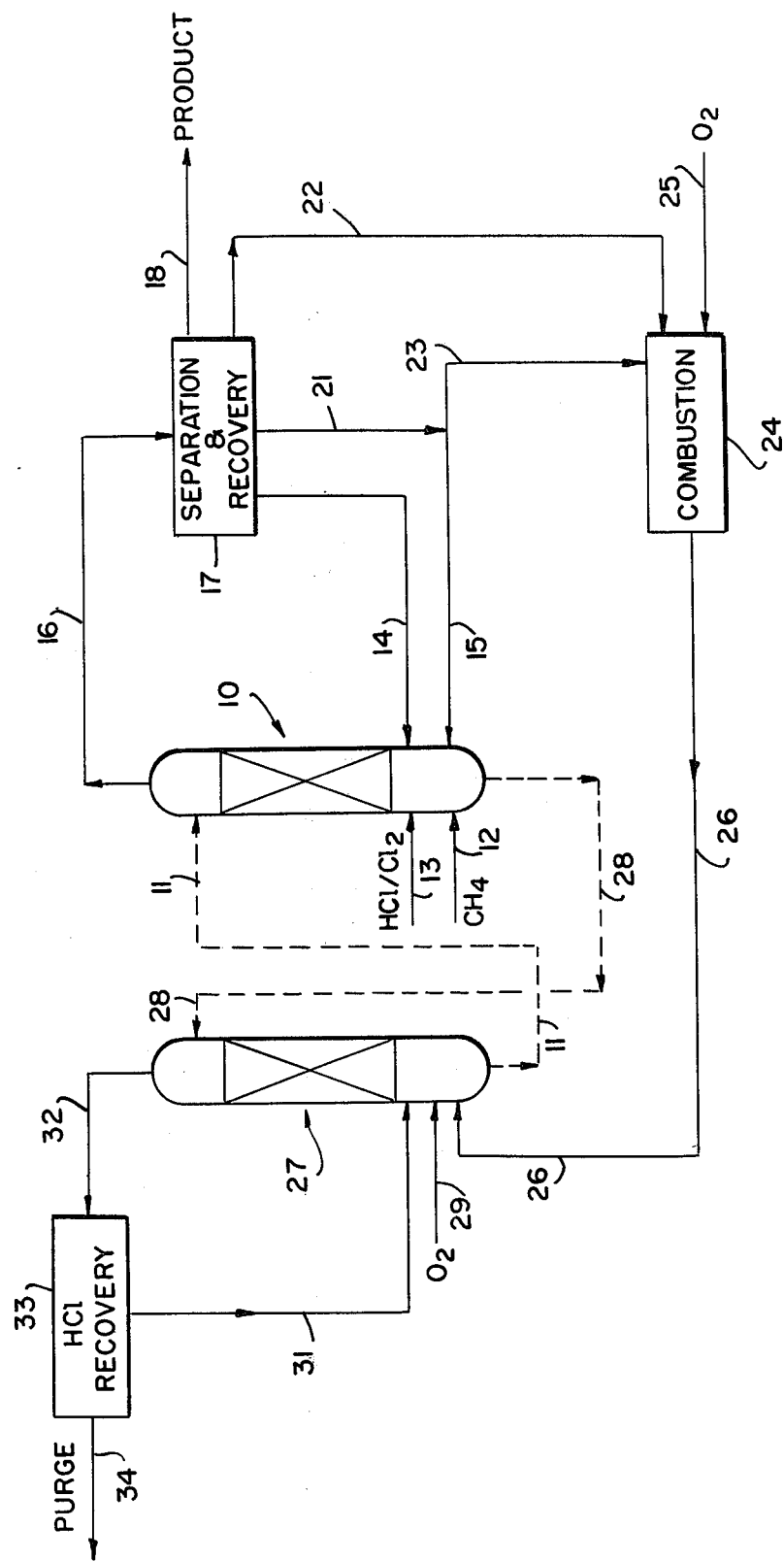

PURGING OF INERTS IN CHLORINATED HYDROCARBON PRODUCTION

This invention relates to the production of chlorinated hydrocarbons, and more particularly, to a new and improved process for purging inerts from a chlorinated hydrocarbon production system.

In the production of chlorinated hydrocarbons, inerts such as nitrogen and/or carbon monoxide and/or carbon dioxide are generally present in the chlorinated hydrocarbon effluent. In order to prevent a build-up of such inerts, it is necessary to purge such inerts from the system. Such inert purging systems are disclosed, for example, in U.S. Pat. No. 3,980,723 and U.S. Pat. No. 3,988,383.

The present invention is directed to an improved process for effecting purging of inerts from a chlorinated hydrocarbon production system.

In accordance with the present invention, a purge stream, containing unreacted hydrocarbon feed, and inerts, is recovered from a chlorinated hydrocarbon production effluent. The purge stream is employed as a fuel for the system, whereby the fuel values of the unreacted hydrocarbon present in the purge stream are recovered, followed by purging of the inerts from the system.

The chlorinated hydrocarbon effluent may be produced by any one of a wide variety of processes known in the art, including both direct chlorination and oxidative or oxychlorination processes. In general, the direct chlorination process can be effected in the presence or absence of a catalyst, whereas the so-called oxidative or oxychlorination processes are effected in the presence of a Deacon or oxychlorination type of catalyst. The general processes for producing chlorinated hydrocarbon by both chlorination and oxychlorination are well known in the art, and no detailed description thereof is deemed necessary for a complete understanding of the present invention.

Although the process of the present invention is generally applicable to the chlorination and/or oxychlorination of hydrocarbons, the process is particularly suitable for the oxychlorination of $C_1$ to $C_4$ aliphatic hydrocarbons, and in particular, to the oxychlorination of methane to produce chlorinated methane(s); and ethane to produce chlorinated $C_2$ hydrocarbons.

In accordance with the preferred process, a molten mixture containing the higher and lower valent chlorides of a multivalent metal, and in particular cuprous chloride and cupric chloride, and a suitable melting point depressant, such as, potassium chloride, is oxidized in a first reaction zone, and the oxidized molten salt mixture is employed in a second reaction zone to produce the chlorinated hydrocarbon.

In general, the first reaction (oxidation) zone is operated at a temperature of from about 700° F. to about 950° F., and preferably from 800° F. to 900° F., the operating pressure generally being in the order of from 1 to 10 atm. The second reaction zone (chlorinated hydrocarbon production) is generally operated at a temperature of from 700° F. to 1200° F., preferably 700° F. to 950° F. and at operating pressures in the order of from 1 to 10 atm.

Particular processes for producing chlorinated methanes by the use of molten salts are described in U.S. application Ser. No. 299,848, filed on Oct. 24, 1972, and U.S. application Ser. No. 299,114, filed on Oct. 19, 1972. Similarly, processes for producing $C_2$ chlorinated hydrocarbons are described in U.S. Pat. No. 3,879,482 and U.S. Pat. No. 3,937,744.

As hereinabove noted, the gaseous purge stream includes unreacted hydrocarbons and inerts which may be carbon monoxide and/or carbon dioxide and/or nitrogen. The carbon dioxide and/or carbon monoxide are present in the effluent from the chlorinated hydrocarbon production zone as a result of oxidation of hydrocarbon feed. The nitrogen may be present as a result of introduction of air, when employing a direct oxidative chlorination process, or may be present in the effluent as a result of nitrogen or air being employed as a carrier gas for introducing molten salt into the reaction zone. The purge stream may also include some chlorinated hydrocarbon product.

The purge stream is employed in an amount to provide for effective purging of net nitrogen, carbon monoxide and carbon dioxide produced in the chlorinated hydrocarbon production. The purge stream may be recovered from the chlorinated hydrocarbon effluent by any one of a wide variety of procedures. In general, the chlorinated hydrocarbon effluent also includes water vapor, and a convenient method of separating the water vapor from the effluent gas is by cooling to condense water vapor therefrom, with such cooling generally resulting in the condensation of heavier chlorinated hydrocarbon components from the gaseous effluent, whereby a gaseous stream containing unreacted hydrocarbon, inerts and generally also some lighter chlorinated hydrocarbons is recovered from the cooling operation. A portion of such gaseous stream may be employed as the purge gas stream, with the remainder of such stream being recycled to the chlorinated hydrocarbon production zone. In general, such a gaseous stream can be recovered by cooling the chlorinated hydrocarbon effluent in one or more cooling stages, which can be indirect cooling stages or direct quench cooling, to a temperature from about 40° F. to about 100° F., at pressures in the order of from about 190 psig to about 400 psig.

Although the above operation is preferred, it is to be understood that the gaseous stream containing unreacted hydrocarbon and inerts can be recovered by other means; e.g., fractionation.

In the production of chlorinated hydrocarbons, there is generally also produced chlorinated hydrocarbons which are not readily marketable, and such chlorinated hydrocarbon waste by-products are generally subjected to combustion to recover the chlorine values thereof as gaseous chlorine and/or hydrogen chloride. In accordance with a preferred embodiment of the present invention, the purge gas stream is employed as a fuel for such combustion, whereby the fuel values of the purge stream are recovered prior to purging inerts from the system, with such inerts being purged in conjunction with other purged components present in the combustion effluent. The combusion of chlorinated hydrocarbons in order to recover chlorine values therefrom, as hydrogen chloride and/or chlorine is described in U.S. Pat. No. 3,548,016, which is hereby incorporated by reference. In accordance with the present invention, methane present in the purge gas stream is employed to provide fuel values for such combustion.

The invention will be further described with respect to an embodiment thereof illustrated in the accompanying drawing, wherein:

The drawing is a simplified schematic flow diagram of an embodiment of the present invention.

Although the embodiment is particularly described with respect to the production of chlorinated methanes, it is to be understood that the scope of the invention is not limited to such chlorinated methane production.

Referring now to the drawing, a molten salt mixture, containing a multivalent metal chloride in its higher and lower valent state, and further containing the oxychloride of the multivalent metal, as well as a suitable melting point depressant, such as a mixture of cuprous chloride, cupric chloride and copper oxychloride, with potassium chloride as a melting point depressant, is introduced into a chlorinated methane production reactor, schematically indicated as 10 through line 11. The molten salt mixture is obtained as hereinafter described. Fresh feed methane in line 12, hydrogen chloride and/or chlorine in line 13, as well as recycle chlorinated methanes, if required, in line 14 and a recycle methane stream in line 15, are introduced into reactor 10. Reactor 10 is operated at temperatures and pressures to effect oxychlorination of the methane, as well as conversion of recycle chlorinated methanes, to desired chlorinated methane products.

A chlorinated methane production effluent is withdrawn from reactor 10 through line 16. The effluent in line 16 contains chlorinated methanes, unreacted methane, and heavy waste chlorinated materials, such as chlorinated dimers, as well as inerts, which are carbon monoxide and/or carbon dioxide, and which may further contain nitrogen, if nitrogen is employed as a carrier gas for transportation of the molten salt. The effluent in line 16 is introduced into a separation and recovery zone schematically generally indicated as 17.

In separation and recovery zone 17, by procedures known in the art, chlorinated methane product is recovered through line 18. In addition, recycled chlorinated methanes are recovered for recycle to reactor 10 through line 14. Furthermore, by procedures known in the art, there is obtained a methane recycle stream, in line 21, which includes the inerts, as well as some chlorinated methanes. In addition, chlorinated waste byproducts are recovered through line 22. The separation and recovery zone 17 generally includes suitable cooling functions, as well as fractional distillation towers for effecting the desired recovery. In view of the fact that such procedures are generally known in the art, no further details in this respect are deemed necessary for a complete understanding of the present invention.

The recycle methane stream recovered in line 21, which also includes the inerts, as well as some chlorinated methanes, is divided into a purge stream in line 23, as well as a recycle stream for recycle to reactor 10 through line 15. The purge stream 23 is employed to prevent a build up of inerts in the system.

The purge stream in line 23, as well as waste chlorinated byproducts in line 22 are introduced into a combustion zone, schematically generally indicated as 24, along with molecular oxygen in line 25. The combustion zone is operated at conditions known in the art (generally a temperature of 1000° F. to 3000° F. and a pressure of from 1-30 atm) in order to effect combustion of the chlorinated byproducts to recover the chlorine values thereof as gaseous hydrogen chloride and/or chlorine. The methane present in the purge stream in line 23 provides at least a portion of fuel requirements for such combustion. In the event that methane is present in line 23 in excess of such fuel requirements, such methane is combusted and the heat values thereof can be recovered in suitable heat recovery equipment.

A combustion effluent is withdrawn from combustion zone 24 through line 26 and such combustion effluent includes gaseous chlorine values recovered from the chlorinated byproducts in the form of hydrogen chloride and/or chlorine, as well as inerts introduced with the purge stream. In addition, such combustion effluent may contain some unreacted oxygen, and if such oxygen is provided as air, nitrogen is also present in the combustion effluent. Such combustion effluent is introduced into an oxidation reaction zone, schematically generally indicated as 27 in order to recover the chlorine values therefrom.

Molten salt withdrawn from the chlorinated methane production zone 10 through line 28 is introduced into the oxidation reactor 27 wherein the molten salt is contacted with the combustion effluent introduced through line 26, molecular oxygen introduced through line 29, and recycle aqueous hydrogen chloride introduced through line 31. As a result of such contact, the molten salt is oxidized to produce copper oxychloride, and chlorine values present in the streams introduced through lines 26 and 31 are recovered by enriching the cupric chloride content of the molten salt. The molten salt, containing oxychloride, and enriched in cupric chloride is passed to the chlorinated methane production reactor 10 through line 11.

An oxidation reaction effluent is withdrawn from oxidation reactor 27 through line 32, and such effluent contains equilibrium amounts of hydrogen chloride, water vapor, nitrogen and inerts. The effluent in line 32 is introduced into a hydrogen chloride recovery zone, schematically indicated as 33, wherein aqueous hydrogen chloride is recovered for recycle to the oxidation reactor 27 through line 31. Such hydrogen chloride recovery can be effected as known in the art; e.g., as disclosed in U.S. Pat. No. 3,968,200. The remainder of the effluent is withdrawn from the hydrogen chloride recovery zone through line 34 and after neutralization of any remaining hydrogen chloride may be purged to the atmosphere.

Although the invention has been described with respect to a specific embodiment illustrated in the drawing, the invention is not limited to such an embodiment. Similarly, such embodiment may be modified within the spirit and scope of the present invention. Thus, for example, if the content of chlorinated methanes present in the purge gas warrants separation thereof prior to introduction into the combustion zone, such chlorinated methanes may be separated by an absorption process, with such chlorinated methanes then being either recycled to the chlorinated methane production reactor and/or to the separation and recovery zone.

The present invention is particularly advantageous in that it is possible to effectively purge inerts from a chlorinated hydrocarbon production system without the necessity of employing a complicated absorption and stripping system, and with effective utilization of hydrocarbon values. In accordance with the present invention, any hydrocarbon values present in the purge stream are effectively utilized to provide fuel and/or heating values to the system.

Numerous modifications and variations of the present invention are possible in light of the above teachings and, therefore, within the scope of the appended claims the invention may be practised otherwise than as particularly described.

I claim:

1. In a process for producing a chlorinated hydrocarbon from a $C_1$ to $C_4$ aliphatic hydrocarbon in a chlorinated hydrocarbon production zone wherein the effluent withdrawn from the chlorinated hydrocarbon production zone includes inert gas, the improvement comprising:

recovering an effluent from the chlorinated hydrocarbon production zone containing chlorinated hydrocarbon, inert gas, unreacted hydrocarbon and waste chlorinated byproduct;

recovering from the effluent a gas recycle stream containing unreacted hydrocarbon and the inert gas present in the effluent, a portion of which is recycled to the chlorinated hydrocarbon production zone;

recovering chlorinated hydrocarbon from the effluent;

recovering waste chlorinated byproducts from the effluent;

combusting waste chlorinated byproducts, said combustion employing the remaining portion of the gas recycle stream to recover hydrocarbon fuel values, said remaining portion of the gas recycle stream used in the combustion provides for purging of the net inert gas from the effluent subsequent to said combustion, said combustion producing a gaseous combustion effluent, said gaseous combustion effluent containing chlorine values and the inert gas;

separating from the combustion effluent chlorine values and a gas containing the inert gas; and purging the gas containing the inert gas from the system.

2. The process of claim 1 wherein the hydrocarbon is ethane.

3. The process of claim 1 wherein the hydrocarbon is methane.

4. The process of claim 1 wherein the inert gas is comprised of at least one member selected from the group consisting of carbon monoxide, carbon dioxide and nitrogen.

5. In a process for producing chlorinated methanes wherein a molten salt mixture, containing the higher and lower valent chlorides of a multivalent metal is oxidized in a first reaction zone and the oxidized molten salt mixture is employed in a second reaction zone to produce chlorinated methanes, an improved process, comprising:

recovering from the second reaction zone an effluent containing chlorinated methanes, inert gas, unreacted methane and waste chlorinated byproducts;

recovering from the effluent a gas recycle stream containing unreacted methane and the inert gas present in the effluent, a portion of which is recycled to the second reaction zone;

recovering chlorinated methanes from the effluent;

recovering waste chlorinated byproduct from the effluent;

combusting waste chlorinated byproduct, said combustion employing the remaining portion of the gas recycle stream to recover methane fuel values, said remaining portion of the gas recycle stream used in the combustion provides for purging of the net inert gas from the effluent subsequent to said combustion, said combustion producing a gaseous combustion effluent containing chlorine values and the inert gas;

introducing combustion effluent into the first reaction zone to recover chlorine values therefrom;

recovering a gas stream containing the inert gas from the first reaction zone; and purging the gas stream containing the inert gas from the system.

6. The process of claim 5 wherein the multivalent metal is copper.

7. The process of claim 5 wherein the gas recycle stream is recovered from the effluent by cooling the effluent to condense chlorinated methanes.

* * * * *